United States Patent [19]

Taparia

[11] Patent Number: 6,085,751
[45] Date of Patent: Jul. 11, 2000

[54] ANIMAL PILL MAGNET

[75] Inventor: Sharad Taparia, Mumbai, India

[73] Assignee: Taparia Magnetics Pvt. Limited, Mumbai, India

[21] Appl. No.: 09/305,624

[22] Filed: May 5, 1999

Related U.S. Application Data

[60] Provisional application No. 60/091,780, Jul. 6, 1998.
[51] Int. Cl.$^7$ .............................. A61B 19/00; H01F 7/02
[52] U.S. Cl. .......................... 128/897; 335/302; 335/306
[58] Field of Search .................................... 600/12, 9–15, 600/3, 8; 335/302–306; 128/897, 898; 210/222; 424/453; 425/804

[56] References Cited

U.S. PATENT DOCUMENTS

| | | |
|---|---|---|
| 3,187,239 | 6/1965 | Rosenberger et al. . |
| 4,283,698 | 8/1981 | Fujisawa ................................. 335/306 |
| 4,303,062 | 12/1981 | Vars . |
| 4,749,978 | 6/1988 | Imamura et al. ........................ 335/284 |
| 4,810,987 | 3/1989 | Liebthal et al. ......................... 335/302 |
| 4,992,768 | 2/1991 | Mozis et al. ............................ 335/306 |
| 5,096,763 | 3/1992 | Ogata et al. . |
| 5,128,644 | 7/1992 | Nellessen ................................ 335/306 |
| 5,663,701 | 9/1997 | Kaura . |
| 5,905,425 | 5/1999 | Dalby et al. ............................ 335/302 |

*Primary Examiner*—Cary O'Connor
*Assistant Examiner*—Catherine McPherson
*Attorney, Agent, or Firm*—Jenkens & Gilchrist, P.C.

[57] ABSTRACT

An animal pill magnet having a casing, core pieces, and at least one magnet. The casing comprises a first capsule half and a second capsule half that are joined together with a single joint to enclose the core pieces and at least one magnet.

15 Claims, 3 Drawing Sheets

ANIMAL PILL MAGNET

This application claims benefit of Provisional Appl. 60/091,780 filed Jul. 6, 1998.

BACKGROUND

1. Field of the Invention

The present invention relates to Animal Pill type magnets for collection of iron bearing debris in the stomach of animals.

2. History of the Related Art

The prior art teaches the use of magnets for collecting debris in an animal's stomach. An example of this prior art is U.S. Pat. No. 5,663,701, titled Stomach Debris Collection Magnet, issued to Kaura on Sep. 2, 1997, which is incorporated in its entirety herein by reference thereto. As taught by Kaura, it is preferable to incase the magnetic device so that gastric juices in the stomach of the animal will not cause corrosion of the device. However, the encasement of the magnetic device can influence the operation of the magnetic field on iron bearing objects ingested by the animal. Therefore, there is a need for an animal pill magnet with an improved casement.

SUMMARY OF THE INVENTION

In one embodiment, the present invention comprises an animal pill magnet having a casing, a first and a second core end piece, a first and a second magnet, and a central center core. The casing includes a first capsule half having a first capsule chamber with a first capsule open end and a first capsule hollow bottom, a second capsule half having a second capsule chamber with a second capsule open end and a second capsule hollow bottom, where the first capsule open end is secured adjacent to the second capsule open end to form a single joint. The first core end piece has a first core end piece first surface and a first core end piece second surface, where the first core end piece first surface is disposed adjacent to the first capsule hollow bottom. The second core end piece has a second core end piece first surface and a second core end piece second surface, where the second core end piece first surface is disposed adjacent to the second capsule hollow bottom. The first magnet has a first magnet first surface and a first magnet second surface, where the first magnet first surface is disposed adjacent to the first core end piece second surface. The second magnet has a second magnet first surface and a second magnet second surface, where the second magnet first surface is disposed adjacent to the second core end piece second surface. The center core has a center core first surface and a center core second surface, where the center core first surface is adjacent to the first magnet second surface and the center core second surface is adjacent to the second magnet second surface.

In another embodiment, the present invention comprises an animal pill magnet having a casing, a first and a second pole piece, and a magnet. The casing includes a first capsule half having a first capsule chamber with a first capsule open end and a first capsule hollow bottom, a second capsule half having a second capsule chamber with a second capsule open end and a second capsule hollow bottom, where the first capsule open end is secured adjacent to the second capsule open end. The first pole piece has a first pole piece first surface and a first pole piece second surface, where the first pole piece first surface is disposed adjacent to the first capsule hollow bottom. The second pole piece has a second pole piece first surface and a second pole piece second surface, where the second pole piece first surface is disposed adjacent to the second capsule hollow bottom. The magnet has a magnet first surface and a magnet second surface, where the magnet first surface is disposed adjacent to the first pole piece second surface and the magnet second surface is disposed adjacent to the second pole piece second surface.

BRIEF DESCRIPTION OF THE DRAWINGS

These and other objectives and features of the invention will become more apparent from the following description and claims taken in connection with the accompanying drawings in which:

DETAILED DESCRIPTION

Figure 1:
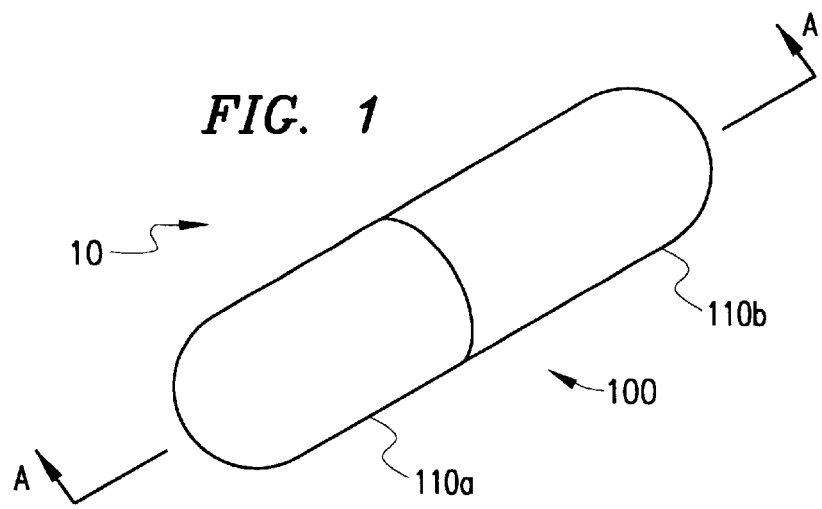
FIG. 1 is a perspective view of the present invention illustrated as an animal pill magnet.
Figure 2:
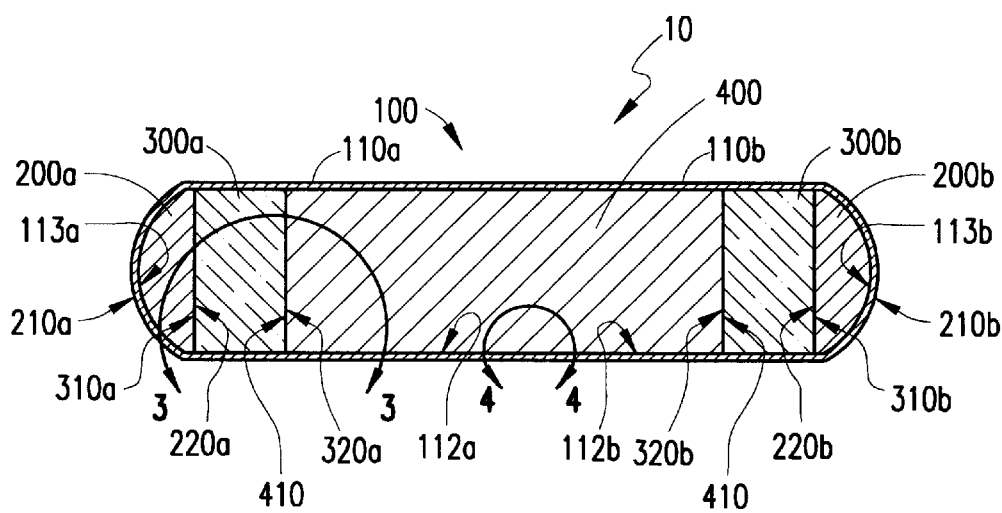
FIG. 2 is a cross-sectional view of one embodiment of the animal pill magnet in FIG. 1, taken about the section lines A—A in FIG. 1.
Figure 3:
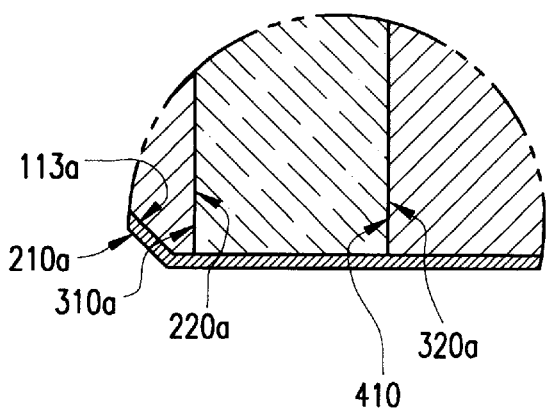
FIG. 3 is an enlarged, partial cross-sectional view of the version of the animal pill magnet in FIG. 2, taken about the sectional lines 3—3.
Figure 4:
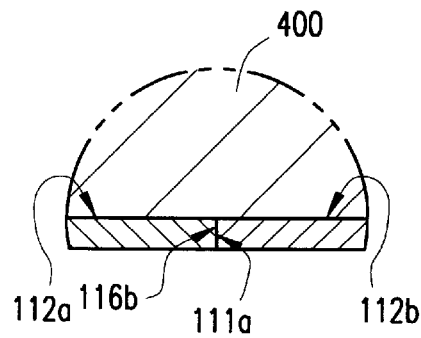
FIG. 4 is an enlarged, partial cross-sectional view of the version of the animal pill magnet in FIG. 2, taken about section lines 4—4.

Referring now to the drawings, and more particularly, to FIG. 1, there is shown an embodiment of the present invention illustrated as the animal pill magnet 10. As shown in FIGS. 2–4, the animal pill magnet 10 generally includes a casing 100, first and second core end pieces 200a and 200b, first and second magnets 300a and 300b, and a center core 400.

The casing 100 comprises a first capsule half 110a and a second capsule half 110b. The first capsule half 110a and the respective second capsule half 110b have cylindrical bodies 112a and 112b, which have open first ends 111a and 111b and which are closed at the second end with concave or hollow bottoms 113a and 113b. In one embodiment, the first capsule half 110a and the second capsule half 110b are formed of 316 stainless steel. The thickness of the first capsule half 110a and the second capsule half 110b is selected to maximize the magnetic field radiating outside the animal pill magnet 10 without causing a risk that the casing 100 will rupture or leak and expose the material inside.

The core end pieces 200a and 200b have end piece first surfaces 210a and 210b, and end piece second surfaces 220a and 220b. In one embodiment, the core end pieces 200a and 200b are formed of a mild steel. The core end pieces 200a and 200b are disposed within the capsule halves 110a and 110b, respectively, with the end piece first surfaces 210a and 210b adjacent to the hollow bottoms 113a and 113b, respectively. In a preferred embodiment, the end piece first surfaces 210a and 210b are a convex surface that match the concave surface of the hollow bottoms 113a and 113b of the capsule halves 110a and 111b.

The magnets 300a and 300b have magnet first surfaces 310a 310b, and magnet second surfaces 320a and 320b. In one preferred embodiment, the magnets 300a and 300b are NdFeB magnets. The magnets 300a and 300b are disposed within the cylindrical bodies 112a and 112b, respectively, of the capsule halves 110a and 110b with the magnet first surfaces 310a and 310b adjacent to the second end surfaces 220a and 220b, respectively, of the core end pieces 200a and 200b. In a preferred embodiment, the magnet first surfaces 310a and 310b match and flushly engage the second end surfaces 220a and 220b, respectively, of the core end pieces 200a and 200b.

The center core 400 has a center core first surface 410 and a center core second surface 420. In one preferred embodiment, the center core 400 is formed of a mild steel. The open ends 111a and 111b of the first capsule end 110a and the second capsule end 110b, respectively, are secured adjacent to each other to enclose the center core 400 within the cylindrical bodies 112a and 112b. Within the cylindrical bodies 112a and 112b, the center core first surface 410 is positioned adjacent to the second surface 320a of the first magnet 300a, and the center core second surface 420 is positioned adjacent to the second surface 320b of the second magnet 300b. In a preferred embodiment, the center core first surface 410 matches and flushly engages the second surface 320a of the first magnet 300a, and the second center core surface 420 matches and flushly engages the second surface 320b of the second magnet 300b.

Figure 5:
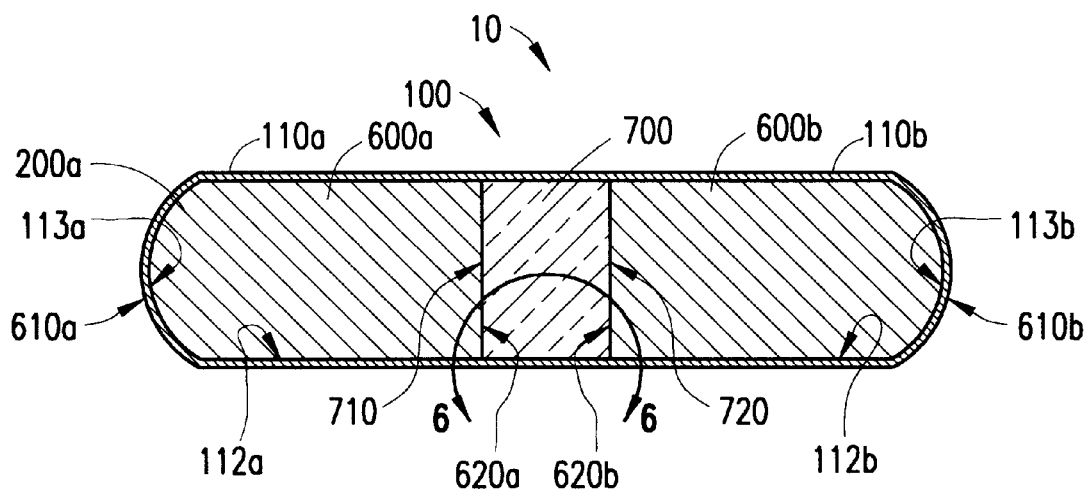
FIG. 5 is a cross-sectional view of one embodiment of the animal pill magnet in FIG. 1, taken about the section lines A—A.
Figure 6:
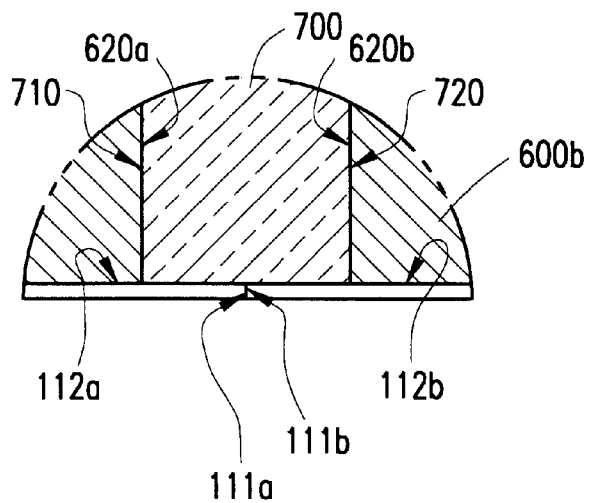
FIG. 6 is an enlarged, partial cross-sectional view of the embodiment of the animal pill magnet in FIG. 5, taken about the section lines 6—6.

Referring now to FIGS. 5 and 6, there is shown another embodiment of the animal pill magnet 10 from FIG. 1. In the embodiment shown in FIGS. 5 and 6, the first and second core end pieces 200a and 200b, the first and second magnets 300a and 300b, and the center core 400 (all shown in FIG. 2) are replaced by a first and second pole piece 600a and 600b and a magnet 700 (as shown in FIG. 5).

The pole pieces 600a and 600b have pole piece first surfaces 610a and 610b, and pole piece second surfaces 620a and 620b. In one embodiment, the pole pieces 600a and 600b are formed of a mild steel. The pole pieces 600a and 600b are disposed within the capsule halves 110a and 110b, respectively, with the pole piece first surfaces 610a and 610b adjacent to the hollow bottoms 113a and 113b of the capsule halves 110a and 110b. In a preferred embodiment, the pole piece first surfaces 610a and 610b are a convex surface that matches the concave surfaces of the hollow bottoms 113a and 113b, respectively, of the capsule halves 110a and 110b.

The center magnet 700 has a center magnet first surface 710 and a center magnet second surface 720. In a preferred embodiment, the center magnet 700 is a NdFeB magnet. The center magnet 700 is disposed within the cylindrical bodies 112a and 112b of the capsule halves 110a and 110b, with center magnet first surface 710 adjacent to the second surface 620a of the first pole piece 600, and the center magnet second surface 720 adjacent to the pole piece second surface 620b of the second pole piece 600b. In one embodiment, the magnet first surface 710 matches and flushly engages the pole piece second surface 620a of the first pole piece 600a, and the center magnet second surface 720 matches and flushly engages the pole piece second surface 620b of the second pole piece 600b.

Referring now to FIGS. 1–6, the open end 111a of the first capsule half 110a is secured adjacent to open end 111b of the second capsule half 110b by an adhesive. The adhesive securing the first capsule half 110a to the second capsule half 110b is uniformly applied on the inside surface of the capsule halves 110a and 110b for securing the animal pill magnet 10 as a unitary whole.

Figure 7:
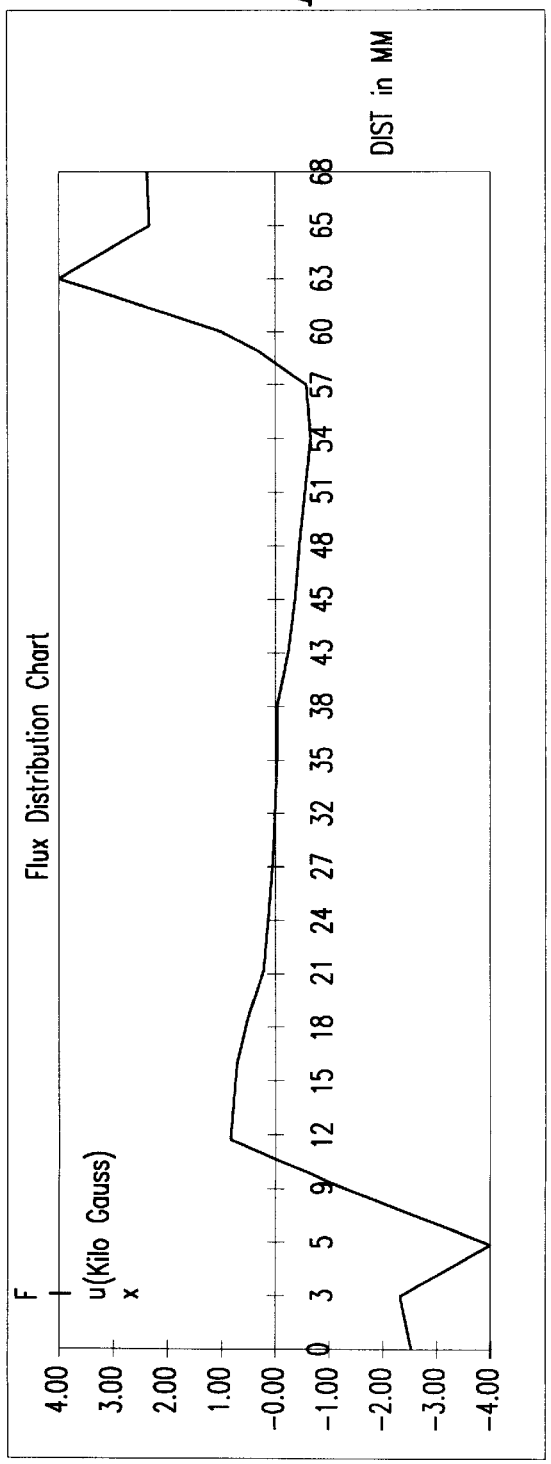
FIG. 7 is a chart showing the magnetic energy over the lateral distance of the animal pill magnet illustrated in the embodiment in FIGS. 2–4.

Referring now to FIG. 7, there is shown a chart of the magnetic energy (in Kilo Gauss), of the embodiment of the animal pill magnet 10 illustrated in FIGS. 2–4, over the lateral distance of the animal pill magnet 10. As shown in FIG. 7, the animal pill magnet 10 has two annular zones of relatively high magnetic strength separated by a dead zone of significant length. A distribution of magnetic flux such as shown in FIG. 7, has the attribute of initially collecting debris in the high zones, and then collecting debris in the dead zone to form a ball that efficiently holds together the debris.

Figure 8:
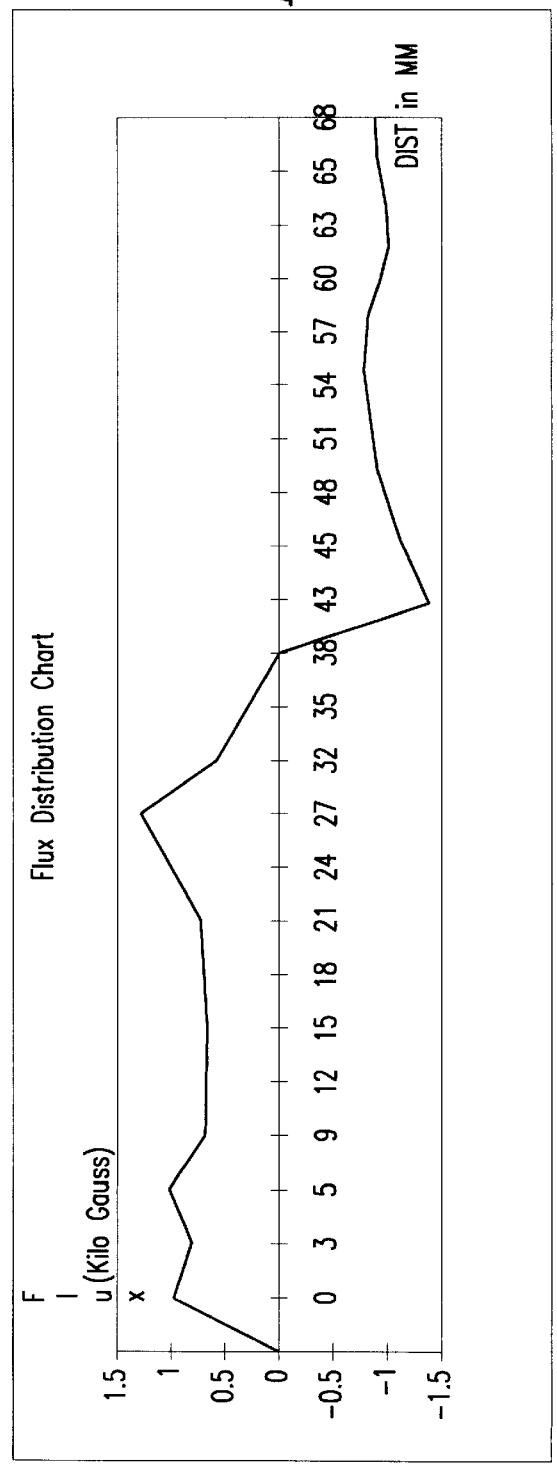
FIG. 8 is a chart showing the magnetic energy over the lateral distance of the animal pill magnet illustrated in the embodiment in FIGS. 5–6.

Referring now to FIG. 8, there is shown a chart of the magnetic energy (in Kilo Gauss), of the embodiment of the animal pill magnet 10 illustrated in FIGS. 5–6, over the lateral distance of the animal pill magnet 10. The magnetic energy distribution in FIG. 8 has less flux leakage as compared to magnetic energy distributions for other animal pill magnets (see e.g. FIG. 7), and therefore the animal pill magnet illustrated in FIGS. 5–6 will have a greater reach. The greater reach of the design of the animal pill magnet 10 illustrated in FIGS. 5–6 will allow the animal pill magnet 10 to pull iron debris from a greater distance.

The present invention has many advantages over the prior art. The number of joints are reduced from two or more in the prior art, down to a single joint. The single joint reduces the chances of the casing will open up after ingestion by an animal or that gastric fluids will enter the assembly of the animal pill magnet 10 and produces deleterious effects. The rounded ends of the capsule housing 112a and 112b encasing the rounded ends of the core/pole pieces are lighter in weight than the more massive separate end caps of the prior pill magnets, exemplified by the Kaura patent structure. The structure of the pill magnets of the present invention reduces the weight of the animal pill magnet 10 over the prior art structure. The reduced weight is healthier for the animal and allows the animal pill magnet to more easily pass the dairyman's test. The dairyman's test consists of placing one animal pill magnet on top of a non-magnet table, (e.g. wooden) approximately one inch in thickness, and a second animal pill magnet underneath the table. If the magnets hold each other in place so that the lower magnet does not fall, the animal pill magnet passes the dairyman's test.

It is thus believed that the operation and construction of the present invention will be apparent from the foregoing description of a preferred embodiment. While the device and method shown are described as being preferred, it will be obvious to a person of ordinary skill in the art that various changes and modifications may be made therein without departing from the spirit and scope of the invention as defined in the following claims. Therefore, the spirit and scope of the appended claims should not be limited to the description of the preferred embodiments contained herein.

What is claimed is:

1. An animal pill magnet, comprising:
 a casing including:
  a first capsule half having a first capsule chamber with a first capsule open end and a first capsule hollow bottom;
  a second capsule half having a second capsule chamber with a second capsule open end and a second capsule hollow bottom; and wherein the first capsule open end is secured adjacent to the second capsule open end;

a first core end piece having a first core end piece first surface and a first core end piece second surface, the first core end piece first surface being disposed adjacent to the first capsule hollow bottom;

a second core end piece having a second core end piece first surface and a second core end piece second surface, the second core end piece first surface being disposed adjacent to the second capsule hollow bottom;

a first magnet having a first magnet first surface and a first magnet second surface, the first magnet first surface being disposed adjacent to the first core end piece second surface;

a second magnet having a second magnet first surface and a second magnet second surface, the second magnet first surface being disposed adjacent to the second core end piece second surface; and a center core having a center core first surface and a center core second surface, the center core first surface being adjacent to the first magnet second surface and the center core second surface being adjacent to the second magnet second surface.

2. The animal pill magnet of claim 1 wherein said first capsule half and said second capsule half are formed of 316 stainless steel.

3. The animal pill magnet of claim 1 wherein said first core end piece and said second core end piece are formed of a mild steel.

4. The animal pill magnet of claim 1 wherein said center core is formed of a mild steel.

5. The animal pill magnet of claim 1 wherein said first magnet and said second magnet are formed of NdFeB.

6. The animal pill magnet of claim 1 wherein said first capsule hollow bottom and said second capsule hollow bottom are concave in shape, and wherein further said first surfaces of said first end piece and said second end piece are convex in shape.

7. The animal pill magnet of claim 1 wherein said first capsule open end is secured adjacent to said second capsule open end by an adhesive.

8. The animal pill magnet of claim 1 wherein said animal pill magnet has two annular zones of relatively high magnetic strength separated by a dead zone of relatively low magnetic strength.

9. An animal pill magnet, comprising:

a casing including:
a first capsule half having a first capsule chamber with a first capsule open end and a first capsule hollow bottom;

a second capsule half having a second capsule chamber with a second capsule open end and a second capsule hollow bottom; and wherein the first capsule open end is secured adjacent to the second capsule open end a first pole piece having a first pole piece first surface and a first pole piece second surface, the first pole piece first surface being disposed adjacent to the first capsule hollow bottom; and a second pole piece having a second pole piece first surface and a second pole piece second surface, the second pole piece first surface being disposed adjacent to the second capsule hollow bottom; and a magnet having a magnet first surface and a magnet second surface, the magnet first surface being disposed adjacent to the first pole piece second surface and the magnet second surface being disposed adjacent to the second pole piece second surface.

10. The animal pill magnet of claim 9 wherein said first capsule half and said second capsule half are formed of 316 stainless steel.

11. The animal pill magnet of claim 9 wherein said first pole piece and said second pole piece are formed of a mild steel.

12. The animal pill magnet of claim 9 wherein said magnet is formed of NdFeB.

13. The animal pill magnet of claim 9 wherein said first capsule hollow bottom and said second capsule hollow bottom are concave in shape, and wherein further said first surfaces of said first pole piece and said second pole piece are convex in shape.

14. The animal pill magnet of claim 9 wherein said first capsule open end is secured adjacent to said second capsule open end by an adhesive.

15. The animal pill magnet of claim 9 wherein said animal pill magnet has reduced flux leakage.

* * * * *